US00PP09140P

United States Patent [19]

Enthoven

[11] Patent Number: Plant 9,140

[45] Date of Patent: May 16, 1995

[54] GERANIUM PLANT NAMED MERITWIN

[75] Inventor: Adrianus W. M. Enthoven, Wateringen, Netherlands

[73] Assignee: Enthoven Breeding B.V., Wateringen, Netherlands

[21] Appl. No.: 197,323

[22] Filed: Feb. 16, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 6,636 2/1989 Winner ..... Plt./87.12

P.P. 7,422 1/1991 Schurmann ..... Plt./87.12

*Primary Examiner*—James R. Feyrer

*Attorney, Agent, or Firm*—Foley & Lardner

[57] ABSTRACT

A new and distinct cultivar of geranium named Meritwin particularly characterized by the combined features of dark green foliage resulting in plants that transport well; compact plant growth habit; double created leaf margins; large inflorescences with many open flowers and buds; large flower diameter; asymmetric flower buds; flowers with 5 to 6 petals; petals with a dark red-purple center and a lighter red-purple margin early and equal flowering; buds that form under low light and single flowers that are rain resistant.

3 Drawing Sheets

The present invention comprises a new and distinct cultivar of geranium, botanically known as *Pelargonium zonale*, and hereinafter referred to by the cultivar name Meritwin.

Meritwin is a product of a planned breeding program which had the objective of creating new geranium cultivars with single flower form, compact habit, fast rooting, good tolerance to Botrytis, superior weather resistance and little need for growth regulators.

Meritwin was originated from a hybridization made by the inventor in a controlled breeding program in Wateringen, The Netherlands in 1987.

The female parent was a proprietary Enthoven seedling Nr. G 221, characterized by its compact growth. The male parent of Meritwin was a proprietary Enthoven seedling Nr. G 34, characterized by its weather resistance.

Meritwin was discovered and selected as one flowering plant within the progeny of the stated cross by Adrianus W. M. Enthoven in June 1988 in a controlled environment in Wateringen, The Netherlands.

The first act of asexual reproduction of Meritin was accomplished when vegetative cuttings were taken from the initial selection in August 1988 in a controlled environment in Wateringen, The Netherlands under the supervision of Adrianus W. M. Enthoven.

Horticultural examination of selected units initiated in the spring and summer of 1989, and continuing thereafter, has demonstrated that the combination of characteristics as herein disclosed for Meritwin are firmly fixed and are retained through successive generations of asexual reproduction.

Meritwin has not been observed under all possible environmental conditions. The phenotype may vary with variations in environment such as temperature, light intensity and day length, without, however, any variation in genotype.

The following measurements and comparisons describe plants grown in Wateringen, The Netherlands under greenhouse and outdoor conditions which approximate those generally used in commercial practice.

The following traits have been repeatedly observed and are determined to be basic characteristics of Meritwin, which in combination distinguish this geranium as a new and distinct cultivar:

1. The growth habit is compact.
2. The foliage is dark green (upper face 147A and lower face 137B) and therefore the plants transport well.
3. The leaf margins are double crenated.
4. The leaf stalks are short and sturdy.
5. The inflorescence is larger with many open flowers and buds.
6. The flower diameter is large.
7. The flowers buds are asymmetric.
8. Each flower has between 5 and 6 petals.
9. The upper surface of the petals has a dark red-purple center and a lighter red-purple margin.
10. Plants flower early and equally.
11. Buds will form under low light.
12. Flowers are single and rain resistant.
13. Due to the compact growth habit the plants do not need any growth regulators during the cultivation period. The plant grows compactly with a height and diameter at maturity equal to approximately 19.4 cm.

Of the many commercial cultivars known to the present inventor, the most similar in comparison to Meritwin is the cultivar Fisrix, disclosed in U.S. Plant Pat. No. 7,422. Reference is made to Chart A which compares certain characteristics of Meritwin to those same characteristics of Fisrix. In general comparison to Fisrix, Meritwin has, among other things, a different flower color on the under surface of the petal and lacks petal zonation.

The accompanying color photographic drawings show typical flower and foliage characteristics of Meritwin, with colors being as true as possible with illustrations of this type.

Sheet 1 is a side view of Meritwin grown in a 10.5 cm pot for approximately 8 weeks showing the foliage, flower stalks and inflorescences.

Sheet 2 is a close-up of the upper and lower sides of a typical leaf from Meritwin.

Sheet 3 is a close-up view of a typical flower from Meritwin showing the flowers from the top and bottom.

In the following description color references are made to The Royal Horticultural Society Colour Chart (RHS) and Horticultural Colour Chart (HCC). The color values were determined between 2.30 and 2.45 p.m. on Jul. 31, 1989 under 21,500 Klux light intensity at Wateringen, The Netherlands.

Classification

*Botanical.*—A hybrid of the genus *Pelargonium zonale* cv. Meritwin.

*Commercial.*—Zonal geranium.

INFLORESCENCE

A. Umbel:

*Average diameter.*—Indoor: 111 mm.

*Average depth.*—Indoor: 89 mm.

*Peduncle length.*—Indoor: 130 mm.

*Pedicel length.—Indoor:* 37 mm.

*Pedicel color.*—Dark red.

B. Corolla:

*Average diameter.*—Indoor: 47 mm.

*Form.*—Single.

*Color (general tonality at a distance of three meters)-.*—RHS 68B, HCC 627/2.

*Color (main body, dark spot, upper surface).*—RHS 57B, HCC 25 with white spot between dark spot and point of attachment of petal.

*Color (near margin upper face).*—RHS 68B, HCC 627/2.

*Under surface ground color.*—RHS 62D with a blush of RHS 62C.

*Color (veins lower surface).*—RHS 62A.

*Diameter lower petals.*—18 mm.

*Length lower petals.*—22 mm.

*Diameter upper petals.*—16 mm.

*Length upper petals.*—22 mm.

*Petal shape.*—Obovate.

*Sepal color.*—Dark veins red green.

C. Bud:

*Shape.*—Asymmetric.

*Color.*—Slightly lighter than corolla.

*Pedical.*—Dark red.

D. Reproductive organs:

*Androecium.*—7–9 anthers.

*Gynoecium.*—4–5 stigma.

E. Spring flowering:

*Response period.*—In Wateringen, The Netherlands in 1989, 60% of plants with at least 1 flower opened 13 weeks after planting unrooted cuttings.

F. Outdoor flower production: The flower count in 1989 in Wateringen, The Netherlands was between 41–46 flowers per plant from June through October observation period.

G. Durability: 80% shatter resistance.

PLANT

A. Foliage:

*Form.*—Kidney shaped with open base.

*Margin.*—Bicrenate.

*Color.*—Dark green.

*Zonation.*—Absent.

B. General appearance and form:

*Internode length.*—25 mm.

*Branching pattern.*—An average of 4.3 branches per plant.

*Height.*—194 mm.

*Diameter.*—194 mm.

C. Tolerance to Botrytis: Good.

CHART A

COMPARISON OF MERITWIN AND FISRIX

| | Meritwin | Fisrix |
|---|---|---|
| Leaf blade: | | |
| Zonation on upperside | absent | present |
| Flower color: | | |
| Under side of petal | RHS 68B, HCC 627/2 | RHS 65A, HCC 527/1 |

I claim:

1. A new and distinct cultivar of geranium plant named Meritwin as illustrated and described.

* * * * *

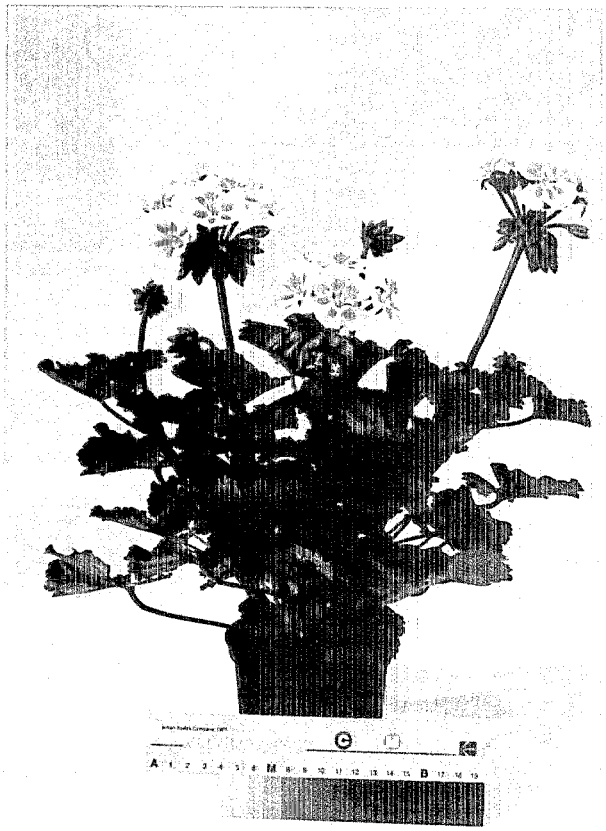

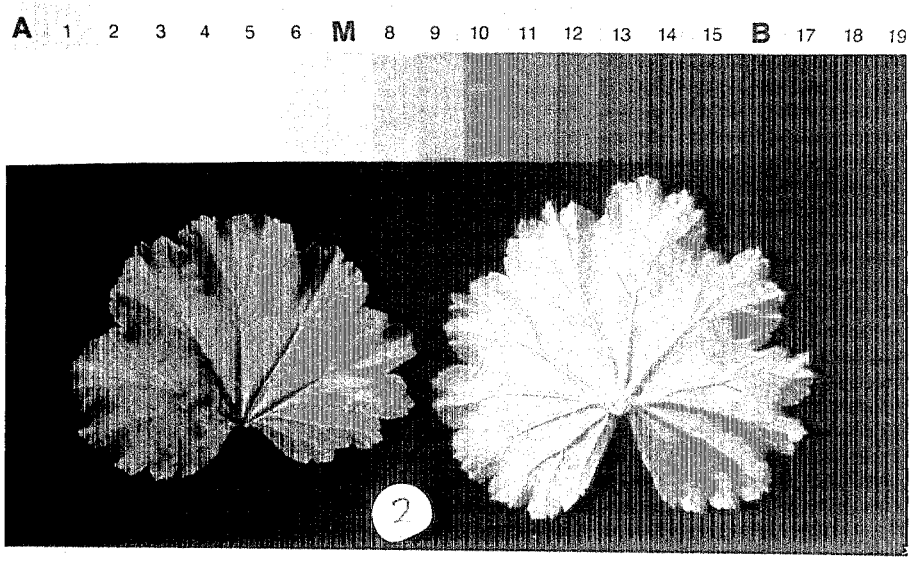
A 1 2 3 4 5 6 M 8 9 10 11 12 13 14 15 B 17 18 19
2

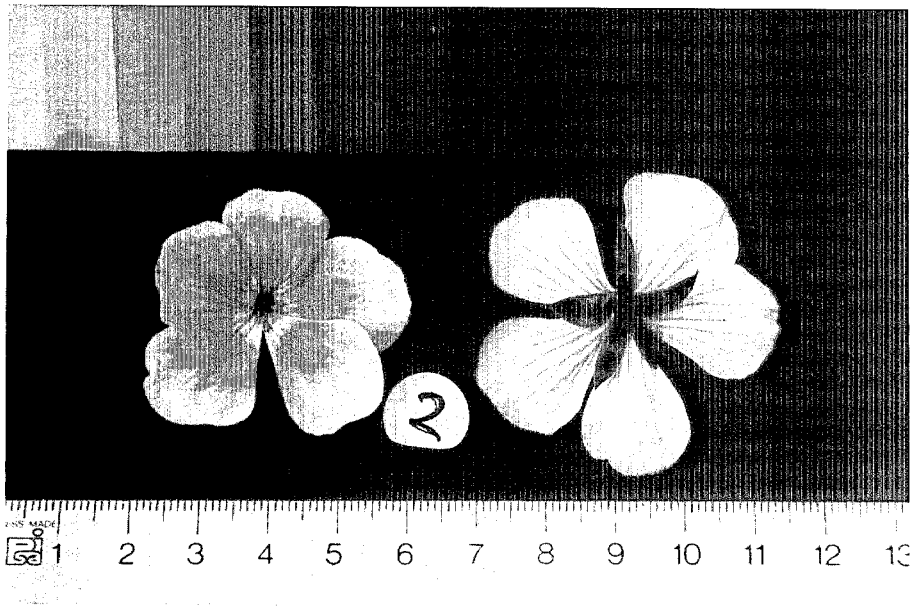
2
1 2 3 4 5 6 7 8 9 10 11 12 13